United States Patent
Wang et al.

(10) Patent No.: US 10,945,991 B2
(45) Date of Patent: Mar. 16, 2021

(54) USE AND PHARMACEUTICAL COMPOSITION FOR LIVER FIBROSIS PREVENTION AND/OR TREATMENT

(71) Applicant: Cojet Biotech Inc., Taipei (TW)

(72) Inventors: Yu-Lung Wang, Taipei (TW); Judy Chen, Taipei (TW)

(73) Assignee: COJET BIOTECH INC., Taipei (TW)

( * ) Notice: Subject to any disclaimer, the term of this patent is extended or adjusted under 35 U.S.C. 154(b) by 71 days.

(21) Appl. No.: 16/173,243

(22) Filed: Oct. 29, 2018

(65) Prior Publication Data

US 2020/0129475 A1 Apr. 30, 2020

(51) Int. Cl.
| | | |
|---|---|---|
| *A61K 31/36* | (2006.01) | |
| *A61K 36/07* | (2006.01) | |
| *A61P 1/16* | (2006.01) | |

(52) U.S. Cl.
CPC .............. *A61K 31/36* (2013.01); *A61K 36/07* (2013.01); *A61P 1/16* (2018.01)

(58) Field of Classification Search
None
See application file for complete search history.

(56) References Cited

FOREIGN PATENT DOCUMENTS

| CN | 105132288 A | 12/2015 |
| JP | 2008-260695 A | 10/2008 |
| TW | 201331362 A1 | 8/2013 |

OTHER PUBLICATIONS

Lien, et al., Molecules, 19:9033. (Year: 2014).*
Yang, et al., Planta Med, 75:512. (Year: 2009).*
Iwakiri, Y., Clinical and Molecular Hepatology, 21:319. (Year: 2015).*
Chen et al., "Antrodia cinnamomea profoundly exalted the reversion of activated hepatic stellate cells by the alteration of cellular proteins," Food and Chemical Toxicology, vol. 69, 2014, pp. 150-162.
Shih et al., "Antrodia cinnamomea reduces carbon tetrachloride-induced hepatotoxicity in male Wister rats," in vivo, vol. 31, 2017, pp. 877-884.

* cited by examiner

*Primary Examiner* — Michael Barker
(74) *Attorney, Agent, or Firm* — Birch, Stewart, Kolasch & Birch, LLP

(57) ABSTRACT

The present disclosure discloses an extract of *Antrodia cinnamomea* and pharmaceutical application thereof. As confirmed by the researches of the present disclosure, said extract of *Antrodia cinnamomea* is able to decrease the activities of hepatic stellate cell and therefore obtain the efficacy of liver fibrosis prevention and/or treatment. Accordingly, the present disclosure discloses a novel pharmaceutical application of *Antrodia cinnamomea* and provides an alternative prevention and/or treatment regime of liver fibrosis for the field.

6 Claims, 14 Drawing Sheets

USE AND PHARMACEUTICAL COMPOSITION FOR LIVER FIBROSIS PREVENTION AND/OR TREATMENT

TECHNICAL FIELD

The present disclosure is related to method and pharmaceutical composition for prevention and/or treatment of liver fibrosis; particularly, is related to method and pharmaceutical composition comprising using *Antrodia cinnamomea* extract for prevention and/or treatment of liver fibrosis.

DESCRIPTION OF RELATED ART

Liver is one of the most important organ in human body, which is composed of parenchymal cells and non-parenchymal cells. Parenchymal cells, also named hepatic cells, contains 60% of the cell population in the liver and 80% of the liver volume. Non-parenchymal cells, on the other hand, is composed of cells providing other biologically importance, including sinusoidal endothelial cell, kupffer cell, hepatic stellate cell and hepatic natural killer cell, which contain 3 to 20% of the population respectively.

Stellate cells, which is also known as Ito cell, locate at the space of Disse (aka perisimusoidal space). Stellate cells are at quiescent stage in the normal condition of liver and provide space for storage of lipid and 90% of vitamin A of the body. When the liver is under inflammation condition, stellate cells would be activated by growth factors and inflammatory cytokine and start to proliferation, producing collagen, releasing stored lipid, secret Vitamin A, and producing and secret cytokines that affect other cells surrounded.

Liver fibrosis is caused by the accumulation of extracellular matrix (ECM) while the liver is suffering chronic damage. The occurrence of liver fibrosis might result from chronic alcohol consumption, virus infection such as HBV or HCV, nonalcoholic steatohepatitis, gene defect, and etc. that might cause structural change of the liver and result in problematic blood supply for liver cells, liver dysfunction, and cirrhosis and tumor eventually.

*Antrodia cinnamomea* is a kind of medicinal fungi, classified as Polyporaceae family, *Antrodia* genus. The fruit body of *Antrodia cinnamomea* has various appearance in shape (such as plate shape, bell shape, horseshoe shape, and tower shape) and color (it is usually bright red at birth and gradually turns into reddish brown, light brown, or light brown). *Antrodia cinnamomea* is an endemic species in Taiwan and is usually found on the hollow heartwood of the trunk of Cinnamomum kanehirai Hay at 200 to 1500 meters altitude.

Prior studies have recognized *Antrodia cinnamomea* in efficacy of detoxification, treating abdominal pain and skin itching. With the development and improvement of extraction and analysis technology, researchers give more and more attention on pharmaceutical application of the components contained in *Antrodia cinnamomea*. A previous study shows that *Antrodia cinnamomea* comprises 5-methyl-benzol[1,3]dioxole-4,7-diol (MBDD), which exhibits potential utility in treating cancer. Further studies suggest MBDD might also provide anti-oxidation ability in removing free radical of 1,1-diphenyl-2-picrylhydrazyl (DPPH) and show slight inhibitory effect on peroxide. Moreover, in the NO production mechanism inducted by lipopolysaccharide, MBDD has proved to reduce the NO production in RAW 264.7 cell line though the result might result from the strong cytotoxicity nature of MBDD (ie. by killing 264.7 cells instead of actually reducing the NO production).

On the other hand, some researches also point out that *Antrodia cinnamomea* extract is capable of inhibiting reactive oxygen species so that is able to inhibit inflammation. Nevertheless, all known pharmaceutical applications of *Antrodia cinnamomea* are silent about preventing and/or treating liver fibrosis. The physiological mechanism of inflammation involves the participation of cyclooxygenase, prostaglandins, interferons, and reactive oxygen species as well as signal transduction thereof. The main cell types involved in this process are monocyte and macrophage. In comparison, the mechanism of fibrosis is about the over-accumulation of connective tissues having stellate cell as the main participant. Inflammation and fibrosis are intrinsically different from each other from the perspective of physiological mechanism. That is to say, even if the inhibitory effect of *Antrodia cinnamomea* on inflammation has already been suggested, the effect of the components of *Antrodia cinnamomea* on hepatic stellate cells is uncertain let alone the effect on preventing and/or treating liver fibrosis.

SUMMARY

One of the objectives of the present disclosure is to provide a method for treating and/or preventing liver fibrosis so that preventing the occurrence of cirrhosis and liver cancer.

Another objective of the present disclosure is to develop the pharmaceutical application of *Antrodia cinnamomea* so that improving the industrial value thereof.

In order to achieve the aforesaid objectives, the present disclosure provides a use of the following Formula (I) compound in preparing a pharmaceutical composition for preventing and/or treating liver fibrosis:

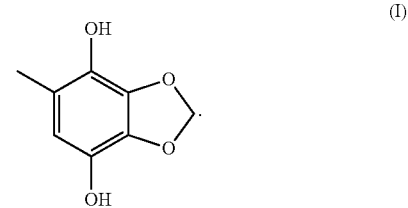

(I)

Preferably, the Formula (I) compound is 5-methyl-benzol[1,3]dioxole-4,7-diol (MBDD). Preferably, the Formula (I) compound is isolated from an *Antrodia cinnamomea* extract. Preferably, the Formula (I) compound is capable of inhibiting the activity of stellate cell.

Preferably, the pharmaceutical composition comprises an effective amount of Formula (I) compound and a pharmaceutically acceptable additive.

Preferably, the pharmaceutical composition is formulated as tablet, capsule, injection, powder, granule, or oral solution.

Preferably, the pharmaceutically acceptable additive comprises: carrier, excipient, preservative, diluent, filler, binding agent, disintegrant, absorption accelerator, sweetener, or a combination thereof.

In another aspect, the present disclosure provides a use of the following Formula (II) compound in preparing a pharmaceutical composition in preventing and/or treating liver fibrosis:

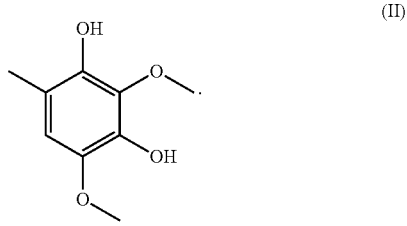

(II)

Preferably, the Formula (II) compound is 2,4-dimethoxy-6-benzene-1,3-diol. Preferably, the Formula (II) compound is isolated from an *Antrodia cinnamomea* extract. Preferably, the Formula (II) compound is capable of inhibiting the activity of stellate cell.

Preferably, the pharmaceutical composition comprises an effective amount of Formula (II) compound and a pharmaceutically acceptable additive.

Preferably, the pharmaceutical composition is formulated as tablet, capsule, injection, powder, granule, or oral solution.

Preferably, the pharmaceutically acceptable additive comprises: carrier, excipient, preservative, diluent, filler, binding agent, disintegrant, absorption accelerator, sweetener, or a combination thereof.

The present disclosure also provides a pharmaceutical composition for preventing and/or treating liver fibrosis comprising an effective amount of Formula (I) compound and/or Formula (II) compound; and a pharmaceutically acceptable additive

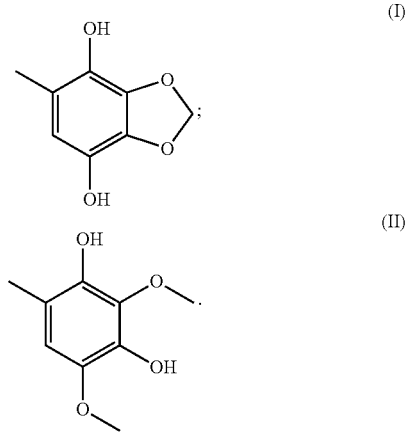

(I)

(II)

Preferably, the Formula (I) compound is 5-methyl-benzol[1,3]dioxole-4,7-diol (MBDD); the Formula (II) compound is 2,4-dimethoxy-6-benzene-1,3-diol.

Preferably, the effective amount is 0.02 to 2.0 g/60 kg body weight/day.

Preferably, the pharmaceutical composition is formulated as tablet, capsule, injection, powder, granule, or oral solution.

Preferably, the pharmaceutically acceptable additive comprises: carrier, excipient, preservative, diluent, filler, binding agent, disintegrant, absorption accelerator, sweetener, or a combination thereof.

Preferably, the pharmaceutical composition comprises 5 to 95 weight percentage of Formula (I) compound and/or Formula (II) compound; wherein the weight percentage is based on the total weight of the pharmaceutical composition.

The present disclosure more provides a use of an *Antrodia cinnamomea* extract in preparing a pharmaceutical composition for preventing and/or treating liver fibrosis; wherein the *Antrodia cinnamomea* extract is prepared by a preparation method; wherein said preparation method comprises the following steps: (a) providing an *Antrodia cinnamomea*; (b) immersing the *Antrodia cinnamomea* in an alcohol solution to obtain a first *Antrodia cinnamomea* extract; wherein the alcohol solution is of 95 to 100% (v/v).

Preferably, the step (a) comprises grinding the *Antrodia cinnamomea* into powder.

Preferably, the step (b) is conducted at 25 to 65° C.

Preferably, the method further comprises drying the first *Antrodia cinnamomea* extract after the step (b) to obtain a powder form of the *Antrodia cinnamomea* extract.

Preferably, the high performance liquid chromatography (HPLC) spectrum of the first *Antrodia cinnamomea* extract exhibits peaks at retention time of 1.66 minute, 2.38 minute, 4.11, minute, 4.42 minute, 7.53 minute, 8.21 minute, 16.48 minute, 17.19 minute, 19.89 minute, 25.79 minute, 31.49 minute, and 38.81 minute; or is as FIG. 1.

Preferably, the method comprises a step (c) for a second second *Antrodia cinnamomea* extract after the step (b); wherein the step (c) is introducing the first *Antrodia cinnamomea* extract through a styrene-based resin column and obtaining the second *Antrodia cinnamomea* extract using ethanol solution as elution buffer; wherein the ethanol solution comprises ethanol of 95 to 100% (v/v) and water at a volume ratio of 1:1.

Preferably, the styrene-based resin column comprises a pore volume of 1 to 2 mL/g. Preferably, the size of the pore of the styrene-based resin column is 200 to 300 Å.

Preferably, the method further comprises drying the second *Antrodia cinnamomea* extract to obtain a powder form of the second *Antrodia cinnamomea* extract after the step (c).

Preferably, the second *Antrodia cinnamomea* extract exhibits the following properties: (i) the high performance liquid chromatography spectrum of the second *Antrodia cinnamomea* extract exhibits peaks at retention time of 1.68 minute, 2.38 minute, 4.10 minute, 4.41 minute, 6.46 minute, 9.58 minute, 17.19 minute, and 19.90 minute; or is as FIG. 2A; (ii) the positive mode LC/MS spectrum of the second *Antrodia cinnamomea* extract exhibits peaks at retention time of 1.80 minute, 2.26 minute, 7.38 minute, 8.73 minute, 10.24 minute, 14.08 minute, 18.64 minute, 19.50 minute, 25.06 minute, 30.16 minute, 32.55 minute, 34.88 minute, 38.54 minute, 48.46 minute, 57.09 minute, 63.79 minute, 68.37 minute, 69.50 minute, and 70.01 minute; or is as FIG. 2B; (iii) the negative mode LC/MS spectrum of the second *Antrodia cinnamomea* extract exhibits peaks at retention time of 2.35 minute, 4.18 minute, 7.72 minute, 11.27 minute, 12.89 minute, 19.29 minute, 23.13 minute, 24.99 minute, 27.36 minute, 27.99 minute, 33.78 minute, 42.40 minute, 42.53 minute, 42.76 minute, 43.12 minute, 43.61 minute, 43.84 minute, 44.90 minute, 48.21 minute, 59.30 minute, 61.97 minute, 64.98 minute, and 71.28 minute; or is as FIG. 2C; and/or (iv) the UV mode LC/MS spectrum of the second *Antrodia cinnamomea* extract exhibits peaks at retention time of 1.25 minute, 5.91 minute, 10.22 minute, 19.29 minute, 23.09 minute, 28.98 minute, 29.21 minute, 29.42 minute, 32.50 minute, 38.18 minute, 42.93 minute, 44.52 minute, 48.37 minute, 54.01 minute, 59.40 minute, and 66.7 minute; or is as FIG. 2D.

Preferably, the method comprises a step (d) for a third *Antrodia cinnamomea* extract after the step (c); wherein the step (d) is introducing the second *Antrodia cinnamomea* extract through a hydroxypropyl sephadex resin column and obtaining the third *Antrodia cinnamomea* extract using methanol solution as elution buffer; wherein the methanol solution comprises methanol of 95 to 100% (v/v) and water at a volume ratio of 1:1.

Preferably, the method further comprises drying the third *Antrodia cinnamomea* extract to obtain a powder form of the third *Antrodia cinnamomea* extract after the step (d).

Preferably, the method comprises a step (e) for a fourth *Antrodia cinnamomea* extract after the step (d); wherein the step (e) is introducing the third *Antrodia cinnamomea* extract through a C18 reverse phase column and obtaining the fourth *Antrodia cinnamomea* extract using methanol solution as elution buffer; wherein the methanol solution comprises methanol of 95 to 100% (v/v) and water at a volume ratio of 1:1.

Preferably, the method further comprises drying the fourth *Antrodia cinnamomea* extract to obtain a powder form of the fourth *Antrodia cinnamomea* extract after the step (e).

Preferably, the method comprises a step (f) for a fifth *Antrodia cinnamomea* extract and a sixth *Antrodia cinnamomea* extract; wherein the step (f) is conducting thin-layer chromatography to the fourth *Antrodia cinnamomea* extract using a methanol solution as mobile phase (running buffer); wherein the methanol solution comprises methanol of 95 to 100% (v/v) and water at a volume ratio of 1:1.

Preferably, the positive mode LC/MS spectrum of the fifth *Antrodia cinnamomea* extract exhibits peaks at retention time of 1.16 minute, 1.96 minute, 2.62 minute, 5.49 minute, 6.31 minute, 8.25 minute, 9.66 minute, 13.07 minute, 13.71 minute, 15.93 minute, 18.30 minute, 21.30 minute, 23.02 minute, 23.73 minute, 25.49 minute, 25.98 minute, 30.17 minute, 31.02 minute, 33.24 minute, 35.29 minute, 35.83 minute, 38.37 minute, and 39.93 minute; or is as FIG. 3A.

Preferably, the positive mode LC/MS spectrum of the sixth *Antrodia cinnamomea* extract exhibits peaks at retention time of 1.67 minute, 2.95 minute, 5.11 minute, 5.60 minute, 7.25 minute, 9.44 minute, 10.45 minute, 12.72 minute, 12.90 minute, 15.50 minute, 17.52 minute, 18.10 minute, 18.54 minute, 19.81 minute, 22.14 minute, 23.62 minute, 21.96 minute, 25.38 minute, 26.52 minute, 28.36 minute, 30.23 minute, 31.01 minute, 31.26 minute, 35.18 minute, 37.48 minute, 38.98 minute, and 39.80 minute; or is as FIG. 4A.

Preferably, the *Antrodia cinnamomea* extract comprises 5-methyl-benzol[1,3]dioxole-4,7-diol of Formula (I) and/or 2,4-dimethoxy-6-benzene-1,3-diol of Formula (II):

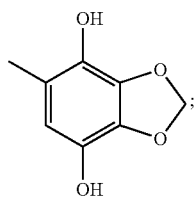

(I)

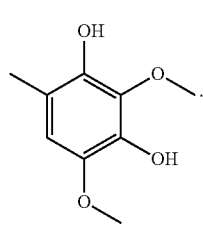

(II)

Preferably, the effective amount of the first *Antrodia cinnamomea* extract for preventing and/or treating liver fibrosis is 0.02 to 2.0 g/60 kg body weight/day.

Preferably, the effective amount of the second *Antrodia cinnamomea* extract for preventing and/or treating liver fibrosis is 0.02 to 2.0 g/60 kg body weight/day.

Preferably, the effective amount of the fifth *Antrodia cinnamomea* extract for preventing and/or treating liver fibrosis is 0.02 to 2.0 g/60 kg body weight/day; and/or the effective amount of the sixth *Antrodia cinnamomea* extract for preventing and/or treating liver fibrosis is 0.02 to 2.0 g/60 kg body weight/day The present disclosure further provides a pharmaceutical composition for preventing and/or treating liver fibrosis, comprising: an *Antrodia cinnamomea* extract and a pharmaceutically acceptable additive; wherein the *Antrodia cinnamomea* extract is selected from a group consisting of the first *Antrodia cinnamomea* extract, the second *Antrodia cinnamomea* extract, the third *Antrodia cinnamomea* extract, the fourth *Antrodia cinnamomea* extract, the fifth *Antrodia cinnamomea* extract, and the sixth *Antrodia cinnamomea* extract.

Preferably, the *Antrodia cinnamomea* extract comprises 5-methyl-benzol[1,3]dioxole-4,7-diol of Formula (I) and/or 2,4-dimethoxy-6-benzene-1,3-diol of Formula (II):

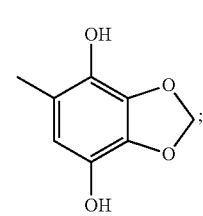

(I)

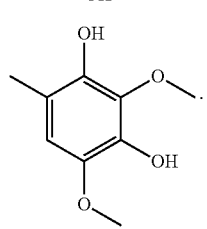

(II)

Preferably, the pharmaceutically acceptable additive comprises carrier, excipient, preservative, diluent, filler, binding agent, disintegrant, absorption accelerator, sweetener, or a combination thereof.

Preferably, the pharmaceutical composition comprises 5 to 95 weight percentage of the *Antrodia cinnamomea* extract; wherein the weight percentage is based on the total weight of the pharmaceutical composition.

Preferably, the pharmaceutical composition is formulated as tablet, capsule, injection, powder, granule, or oral solution.

To sum up, the present disclosure provides a use of a component extracted from *Antrodia cinnamomea* in preparing a pharmaceutical composition for preventing and/or treating liver fibrosis and a pharmaceutical composition comprising the component. The present disclosure successfully utilizes the component extracted from *Antrodia cinnamomea* in a novel pharmaceutical application, that is, preventing/treating liver fibrosis; therefore the present disclosure increases the industrial value of *Antrodia cinnamomea* in pharmaceutical area.

DETAILED DESCRIPTION

Figure 1:
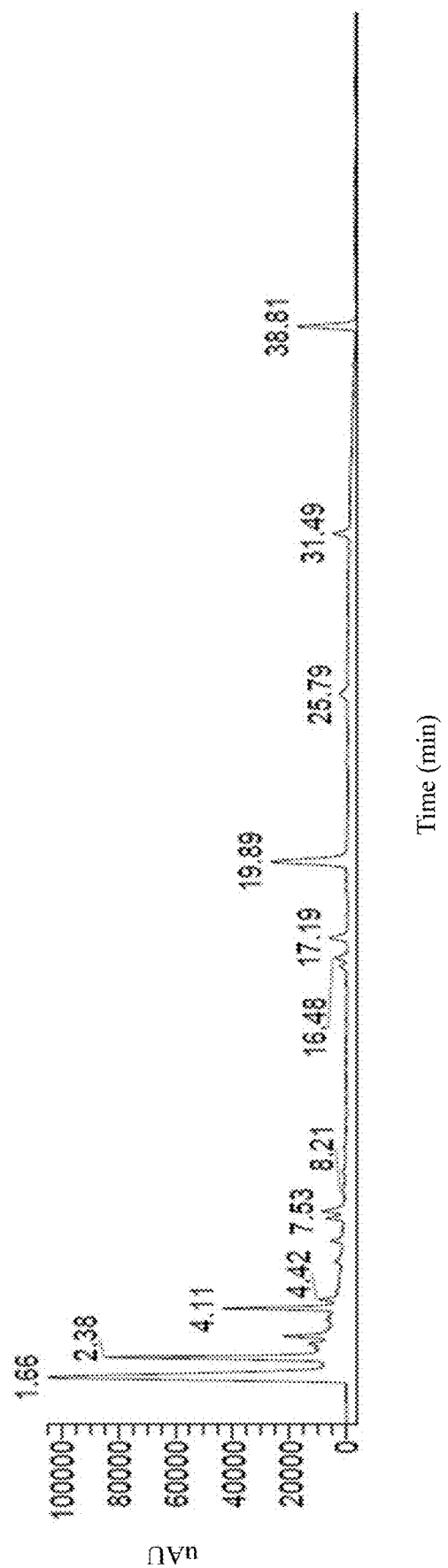
FIG. 1 shows the HPLC spectrum of the first *Antrodia cinnamomea* extract.

The term "preventing/treating" used herein is an abbreviation of preventing and/or treating. The term "preventing", "prevention" "prevent", or alike is referred to prevent a subject from the occurrence of a disease, illness, or harmful symptoms. The term "treating", "treatment" "treat", or alike used herein is referred to obviate, terminate, or reduce the progress of a disease, illness, or harmful symptoms of a subject.

The description "the compound exhibits activity in inhibiting stellate cell" or alike used herein means the compound has negative effect on the growth of stellate cells. By "negative" effect, it could include but not limit to, inhibitory effect on the proliferation of stellate cells, inhibitory effect on the fibrin production of stellate cells, or even killing effect on stellate cells.

One aspect of the present disclosure is related to a pharmaceutical use of *Antrodia cinnamomea* extract. The pharmaceutical use is to use *Antrodia cinnamomea* extract in preparing a pharmaceutical composition for preventing and/or treating liver fibrosis. The *Antrodia cinnamomea* extract is made by the following steps: providing an *Antrodia cinnamomea*; immersing the *Antrodia cinnamomea* in an alcohol solution to obtain a first *Antrodia cinnamomea* extract.

In a preferable embodiment, a fruit body of an *Antrodia cinnamomea* is used for preparing the *Antrodia cinnamomea* extract. In another preferable embodiment, the *Antrodia cinnamomea* is ground; wherein the manner for grinding could be dry grinding or wet grinding. In a preferable embodiment, the alcohol solution could be aqueous ethanol solution.

In an alternative embodiment, the alcohol solution is of a concentration of 50 to 100 (v/v); preferably, of 95 to 100 (v/v). In an alternative embodiment, the immersing of the *Antrodia cinnamomea* in the alcohol solution is conducted at a desirable temperature; preferably, the desirable temperature is 25 to 65° C. In a preferable embodiment, stirring is performed while the immersing step. In an alternative embodiment, the immersing is conducted for 2 to 6 days; preferably, 3 to 5 days.

In a preferable embodiment, the first *Antrodia cinnamomea* extract is introduced through a resin. After that, an alcohol solution is used to elute the resin to obtain a second *Antrodia cinnamomea* extract. In a preferable embodiment, the resin could be a styrene-based resin. In a preferable embodiment, the styrene-based resin column comprises a pore volume of 1 to 2 mL/g. Preferably, the size of the pore of the styrene-based resin column is 200 to 300 Å. In a preferable embodiment, a commercially-available styrene-based resin is used, which includes but not limits to DIAION HP 20 (Mitsubishi Chemical), Amberlite XAD-4 (Rohm & Haas), D101 (Tianjin Nankai HECHENG S&T Co., Ltd). The DIAION HP 20 comprises a pore volume of 1.3 mL/g and a pore size of 260 Å.

In a preferable embodiment, the alcohol solution used for eluting is aqueous ethanol solution. In an alternative embodiment, the alcohol solution is of a concentration of 50 to 100 (v/v); preferably, of 95 to 100 (v/v). In a preferable embodiment, the alcohol solution used for eluting comprises water and alcohol at a ratio of 2:1 to 1:2; more preferable, 1:1.

In a preferable embodiment, the second *Antrodia cinnamomea* extract is introduced through another resin. Then, an alcohol solution is used to elute the resin to obtain a third *Antrodia cinnamomea* extract.

In a preferable embodiment, the resin is a hydroxypropyl sephadex resin. In a preferable embodiment, a commercially-available styrene-based resin is used, which includes but not limits to SEPHADEX LH-20 (GE Healthcare Life Sciences).

In a preferable embodiment, the alcohol solution comprises water and an alcohol; wherein the alcohol is methanol.

In a preferable embodiment, the third *Antrodia cinnamomea* extract is introduced through a C18 reverse phase column. Afterwards, an alcohol solution is used to elute the column to obtain a fourth *Antrodia cinnamomea* extract. In a preferable embodiment, the alcohol solution is as set forth in the preceding paragraphs regarding the third *Antrodia cinnamomea* extract and would not be repeated here.

In a preferable embodiment, a commercially-available C18 reverse phase column is used, including but not limiting to Agilent, XDB-C18 (5 μm, 4.6×150 mm).

In a preferable embodiment, the fourth *Antrodia cinnamomea* extract is applied for thin-layer chromatography using an alcohol solution as mobile phase to obtain a fifth *Antrodia cinnamomea* extract and a sixth *Antrodia cinnamomea* extract. In a preferable embodiment, the alcohol solution is as set forth in the preceding paragraphs regarding the third *Antrodia cinnamomea* extract and the fourth *Antrodia cinnamomea* extract and would not be repeated here. In a preferable embodiment, a commercially-available thin-layer chromatography strip is used; for instance, but not limits to, a silica gel thin-layer strip.

In a preferable embodiment, every *Antrodia cinnamomea* extract obtained in the aforesaid steps is dried. Those having ordinary skill in the art can adopt any common and known method in the field for the drying purpose, for example, by a dryer.

Another aspect of the present disclosure is related to a pharmaceutical composition comprising the *Antrodia cinnamomea* extract of the present disclosure and an additive. The term "effective amount" used herein is referred to an amount that is sufficient to provide the effect of prevention and/or treatment as set forth above. Based on in vitro cell culture study, the effective amount might be defined as "μg/ml"; wherein the calculation depends on the total volume of the cell culture medium used in the culture. Based on animal model study, the effective amount might be defined as "g/60 kg body weight/day". On top of that, the effective amount acquired from a cell culture study can be transformed into a reasonable effective amount for animals by the following calculation:

- Generally, "μg/ml" (effective amount based on in vitro cell culture experiments)="mg/kg body weight/day" (effective amount for mouse); and the metabolism rate of mice is 6 times fast compared to human (Reagan-Shaw et al., 2008).
- Therefore, if the effective amount based on in vitro cell culture experiments is 500 μg/ml, then the effective amount for mouse shall be 500 mg/kg body weight/day (~0.5 g/kg body weight/day). And then the effective amount for human shall be 5 g/60 kg body weight/day after conversion followed abovementioned metabolic rate.
- According the examples in the following paragraphs, the effective amount based on in vitro cell culture experiments is 2.0 to 200 μg/ml; therefore, the reasonable effective amount for human shall be 0.02 to 2.0 g/60 kg body weight/day.

In a preferable embodiment, the additive of the pharmaceutical composition can be selected from carrier, excipient, preservative, diluent, filler, binding agent, disintegrant, absorption accelerator, sweetener, or a combination thereof. The carrier might be water, ethanol, polyol, carboxymethyl cellulose, vegetable oil, organic ester, or a combination thereof. The excipient can be selected from sodium citrate, calcium carbonate, calcium phosphate, or a combination thereof. The preservative used for elongating the shelf life of the pharmaceutical composition includes benzyl alcohol, parabens. The diluent might be selected from water, ethanol, propanediol, glycerol, or a combination thereof. The filler can be selected from lactose, galactose, high molecular weight PEG, or a combination thereof. The binding agent can be selected from sucrose, gelatin, Arabian gum, or a combination thereof. The disintegrant can be selected from potato starch, tapioca starch, silica, or a combination thereof. The absorption accelerator can be selected from DMSO, laurocapram, propylene glycol, glycerol, PEG, or a combination thereof. The sweetener can be selected from Acesulfame K, aspartame, saccharin, sucralose, neotame, or a combination thereof. Except for the aforesaid additives, other additives can be also used in accordance with the actual needs in particular circumstance provided that those additives do not adversely affect the pharmaceutical efficacy of the *Antrodia cinnamomea* extract.

The following examples and embodiments are recited to further interpret the advantages of the present disclosure but not intended to limit the claim scope of the present disclosure.

Experiment 1: Preparation of the First *Antrodia cinnamomea* Extract and the Second *Antrodia cinnamomea* Extract of the Present Disclosure.

(1) Preparation of the extract.

Dry ground or wet ground *Antrodia cinnamomea* powder (Cojet Biotech Inc.) was weighted and mixed with 10-time volume of 95% (v/v) ethanol at 30° C. with stirring for 3 to 5 days. After that, the first *Antrodia cinnamomea* extract was obtained. Then, the first *Antrodia cinnamomea* extract was concentrated by suction filtration to substantially remove any residual ethanol in the extract. The concentrated first *Antrodia cinnamomea* extract was placed for drying in a moisture-proof box and a powder form of the first *Antrodia cinnamomea* extract was eventually obtained. According to a weighting results, the yield rate was 18.53%.

From the first *Antrodia cinnamomea* extract, a second *Antrodia cinnamomea* extract was obtained by chromatography using a styrene-based resin. First of all, styrene-based resin particles (DIAION HP 20, Mitsubishi chemical), which were of 20-time weight to the first *Antrodia cinnamomea* extract, were weighted and immersed with 95% (v/v) ethanol overnight. Afterwards, the immersed resin particles were introduced into an open column and rinsed by ethanol solution (95% (v/v) ethanol:water=1:1). The first *Antrodia cinnamomea* extract powder was restored in 10-time volume of the ethanol solution and introduced into the column. Then, the column was eluted by the ethanol solution of 5-time volume to the styrene-based resin particles. The elution collected was the second *Antrodia cinnamomea* extract of this experiment. Then, the second *Antrodia cinnamomea* extract was concentrated and placed for drying in a moisture-proof box. Then, a powder form of the second *Antrodia cinnamomea* extract was eventually obtained. According to a weighting results, the yield rate was 70.36%.

(2) HPLC Analysis.

Afterwards, HPLC was performed to analyze the first *Antrodia cinnamomea* extract and the second *Antrodia cinnamomea* extract. The subject to be analyzed was restored using mixture solution of methanol, pure water or isopropanol, and acetonitrile (the mixing ratio is about 1:1). The restored solution of the subject to be analyzed was adjusted to have a concentration of 5 mg/mL and put into centrifugation at 13500 rpm for 10 minutes. The supernatant was collected as the sample for the analysis. The conditions of the HPLC performed in this experiment were:

Pump: Spectra SYSTEM P1000; automatic injector: Spectra SYSTEM AS1000; detector: FINNIGAN SURVEYOR PDA Plus; column (immobile phase): Agilent, XDB-C18, 4.6 mm×150 mm, 5 μm; injection volume: 5 μl; flow speed: 0.8 mL/min.

Solvent (Mobile Phase) Gradient:

| Time (minute) | 0.1% formic acid (%) | Acetonitrile (%) |
|---|---|---|
| 0 | 70 | 30 |
| 3 | 60 | 40 |
| 15 | 42 | 58 |
| 21 | 42 | 58 |
| 26 | 35 | 65 |
| 35 | 0 | 100 |
| 50 | 0 | 100 |

The HPLC spectrum of the first *Antrodia cinnamomea* extract is as shown in FIG. 1; wherein the spectrum exhibits peaks at retention time of 1.66 minute, 2.38 minute, 4.11, minute, 4.42 minute, 7.53 minute, 8.21 minute, 16.48 minute, 17.19 minute, 19.89 minute, 25.79 minute, 31.49 minute, and 38.81 minute.

Figure 2A:
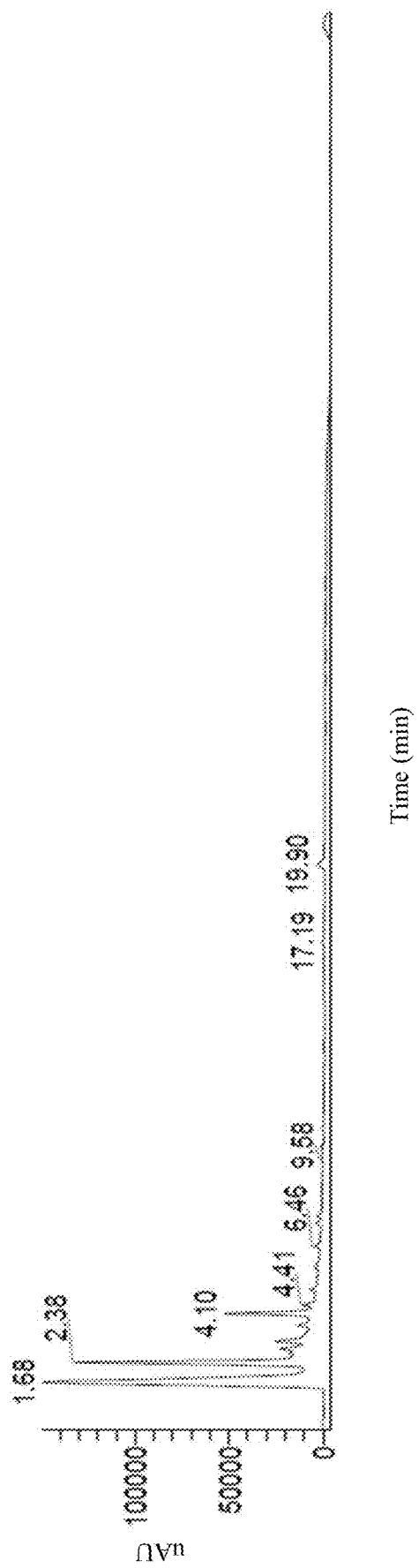
FIG. 2A shows the HPLC spectrum of the second *Antrodia cinnamomea* extract.

The HPLC spectrum of the second *Antrodia cinnamomea* extract is as shown in FIG. 2A; wherein the spectrum exhibits peaks at retention time of 1.68 minute, 2.38 minute, 4.10 minute, 4.41 minute, 6.46 minute, 9.58 minute, 17.19 minute, and 19.90 minute.

(3) LC/MS Analysis.

Furthermore, LC/MS was performed to analyze the first *Antrodia cinnamomea* extract and the second *Antrodia cinnamomea* extract obtained above. The subject to be analyzed was restored by methanol or pure water. The restored solution of the subject to be analyzed was adjusted to have a concentration of 10 mg/mL and put into centrifugation at 13500 rpm for 10 minutes. The supernatant was collected as the sample for the analysis. The conditions of the HPLC performed in this experiment were:

Mass spectrometer: Autosampler (Thermo AS3500); detector: UV 6000LP and LCQ Fleet mass; pump: Thermo P1000; column: Thermo Hyper Carb, 4 mm×100 mm, 5 µm; detector: ESI mass (positive mode or negative mode)/UV 254 nm; injection volume: 10 µl; flow speed: 1.0 mL/min.

Gradient:

| Time (minute) | 0.1% formic acid (%) | Acetonitrile (%) |
| --- | --- | --- |
| 0 | 100 | 0 |
| 25 | 90 | 10 |
| 30 | 70 | 30 |
| 45 | 50 | 50 |
| 60 | 45 | 55 |
| 70 | 0 | 100 |
| 80 | 0 | 100 |

Figure 2B:
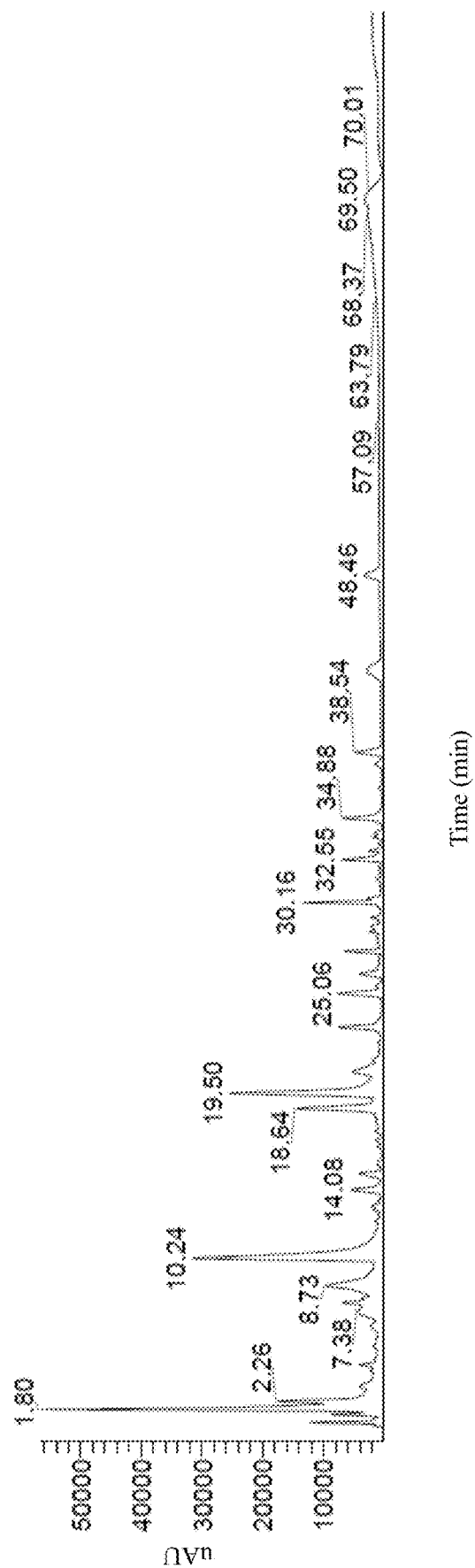
FIG. 2B shows the positive mode LC/MS spectrum of the second *Antrodia cinnamomea* extract.

The positive mode LC/MS spectrum of the second *Antrodia cinnamomea* extract is shown as FIG. 2B; wherein the spectrum exhibits peaks at retention time of 1.80 minute, 2.26 minute, 7.38 minute, 8.73 minute, 10.24 minute, 14.08 minute, 18.64 minute, 19.50 minute, 25.06 minute, 30.16 minute, 32.55 minute, 34.88 minute, 38.54 minute, 48.46 minute, 57.09 minute, 63.79 minute, 68.37 minute, 69.50 minute, and 70.01 minute.

Figure 2C:
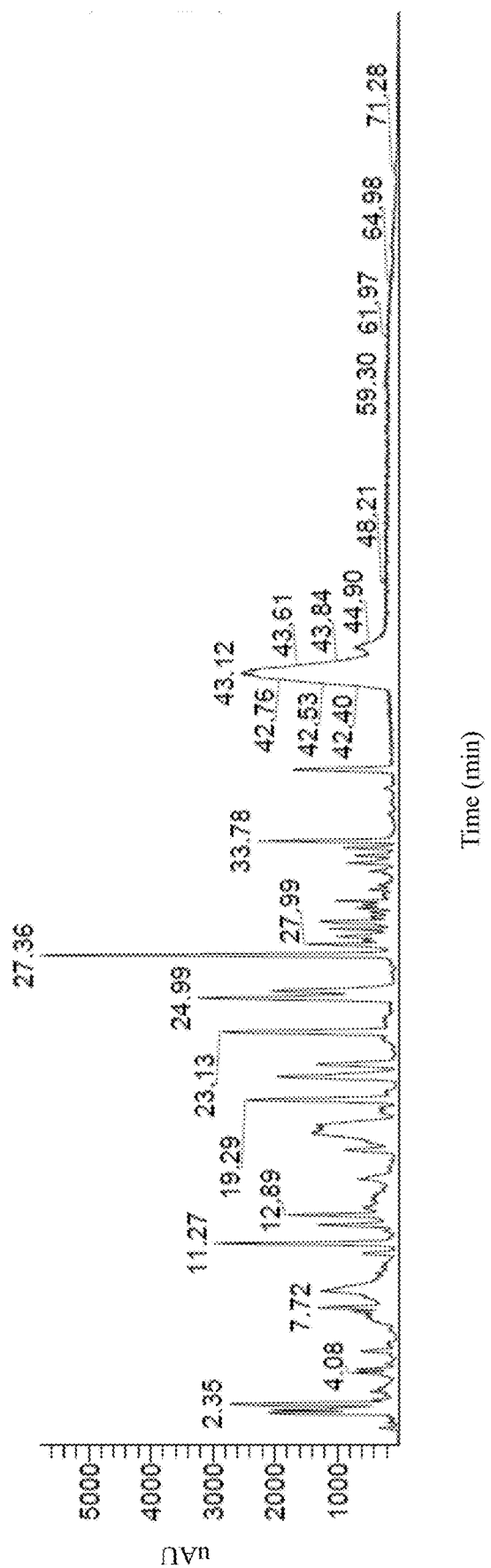
FIG. 2C shows the negative mode LC/MS spectrum of the second *Antrodia cinnamomea* extract.

The negative mode LC/MS spectrum of the second *Antrodia cinnamomea* extract is shown as FIG. 2C; wherein the spectrum exhibits peaks at retention time of 2.35 minute, 4.18 minute, 7.72 minute, 11.27 minute, 12.89 minute, 19.29 minute, 23.13 minute, 24.99 minute, 27.36 minute, 27.99 minute, 33.78 minute, 42.40 minute, 42.53 minute, 42.76 minute, 43.12 minute, 43.61 minute, 43.84 minute, 44.90 minute, 48.21 minute, 59.30 minute, 61.97 minute, 64.98 minute, and 71.28 minute.

Figure 2D:
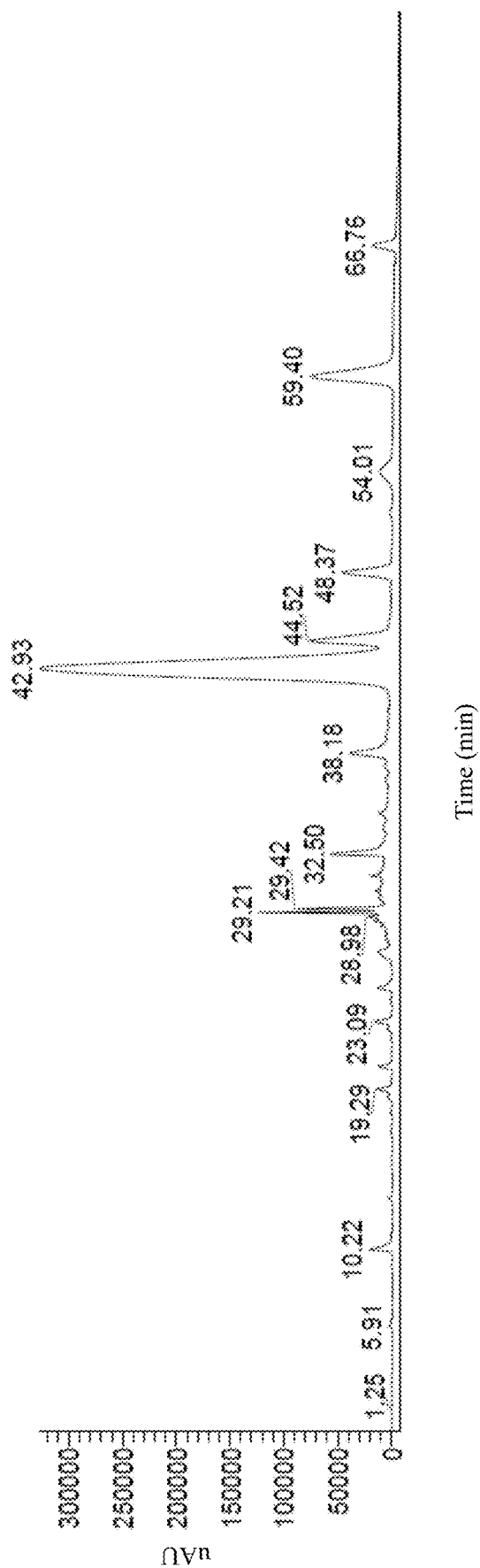
FIG. 2D shows the UV mode LC/MS spectrum of the second *Antrodia cinnamomea* extract.

The UV mode LC/MS spectrum of the second *Antrodia cinnamomea* extract is shown as FIG. 2D; wherein the spectrum exhibits peaks at retention time of 1.25 minute, 5.91 minute, 10.22 minute, 19.29 minute, 23.09 minute, 28.98 minute, 29.21 minute, 29.42 minute, 32.50 minute, 38.18 minute, 42.93 minute, 44.52 minute, 48.37 minute, 54.01 minute, 59.40 minute, and 66.7 minute.

Experiment 2: Preparation of the Third *Antrodia cinnamomea* Extract of the Present Disclosure.

The third *Antrodia cinnamomea* extract was obtained by introducing the second *Antrodia cinnamomea* extract through a hydroxypropyl sephadex resin. First of all, hydroxypropyl sephadex particles (SEPHADEX LH-20; GE Healthcare Life Sciences) were weighted and introducted into an open column. The column was then washed by methanol aqueous solution. Then, the second *Antrodia cinnamomea* extract powder was restored by flash methanol aqueous solution and introduced into the open column. The column was then eluted by the methanol aqueous solution. The elution collected was the third *Antrodia cinnamomea* extract of this experiment. The third *Antrodia cinnamomea* extract was placed for drying in a moisture-proof box. Then, a powder form of the third *Antrodia cinnamomea* extract was eventually obtained.

Experiment 3: Preparation of the Fourth *Antrodia cinnamomea* Extract of the Present Disclosure.

(1) Preparation of the Extract.

The fourth *Antrodia cinnamomea* extract was obtained by introducing the third *Antrodia cinnamomea* extract through a C18 reverse phase column (C18 reversed phase silica gel; Agilent, XDB-C18). First of all, the column was washed by methanol aqueous solution until the column was full of the methanol aqueous solution. Then, the third *Antrodia cinnamomea* extract powder was restored by a small amount of methanol and introduced into the column. Afterwards, the column was eluted by the methanol aqueous solution. The elution collected was the fourth *Antrodia cinnamomea* extract of this experiment. The fourth *Antrodia cinnamomea* extract was placed for drying in a moisture-proof box and then weighted.

Experiment 4: Preparation of the Fifth *Antrodia cinnamomea* Extract and the Sixth *Antrodia cinnamomea* Extract of the Present Disclosure.

(1) Preparation of the Extract.

Thin-layer chromatography was performed to obtain the fifth and the sixth *Antrodia cinnamomea* extract from the fourth *Antrodia cinnamomea* extract. The fourth *Antrodia cinnamomea* extract powder was restored by a small amount of 100% (v/v) methanol. The restored fourth *Antrodia cinnamomea* extract was extended on a 20×20 cm of thin-layer chromatography strip (TLC aluminium sheets, silica gel 60 F254, Merck) using methanol solution (100% (v/v) methanol:water=1:1). Two color bands can be observed under the short wavelength 254 nm ultraviolet light. The areas of the strip corresponding to the two color bands were cut off respectively and immersed in methanol for 10 minutes. The components on the color bands were dissolved in methanol and then suction filtration was performed to remove the methanol. The immersing step of the strip was repeated three times. Afterwards, two components were obtained respectively, which are the fifth and the sixth *Antrodia cinnamomea* extract of this experiment.

LC/MS Analysis.

LC/MS was performed to analyze the fifth *Antrodia cinnamomea* extract and the sixth *Antrodia cinnamomea* extract obtained above. The experiment conditions were as set forth in the Experiment 1 and not repeated here.

Figure 3A:
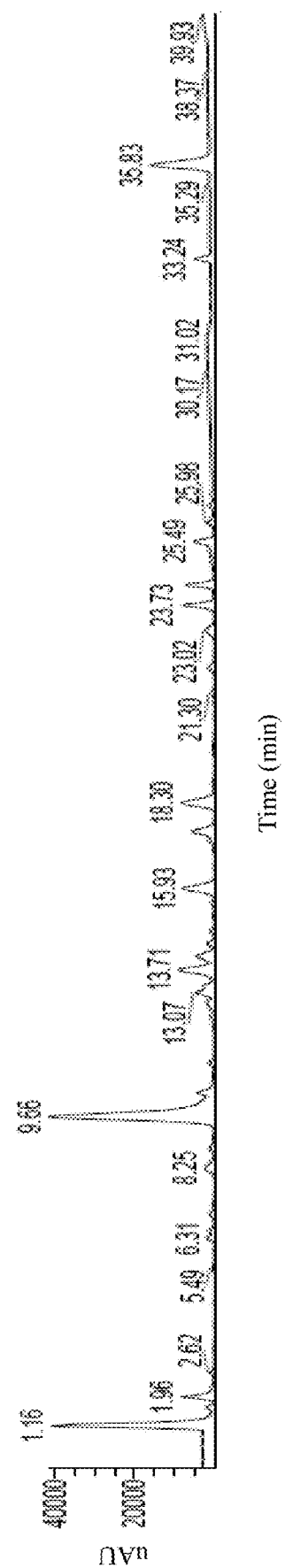
FIG. 3A shows the LC spectrum of the positive mode LC/MS of the fifth *Antrodia cinnamomea* extract.
Figure 3B:
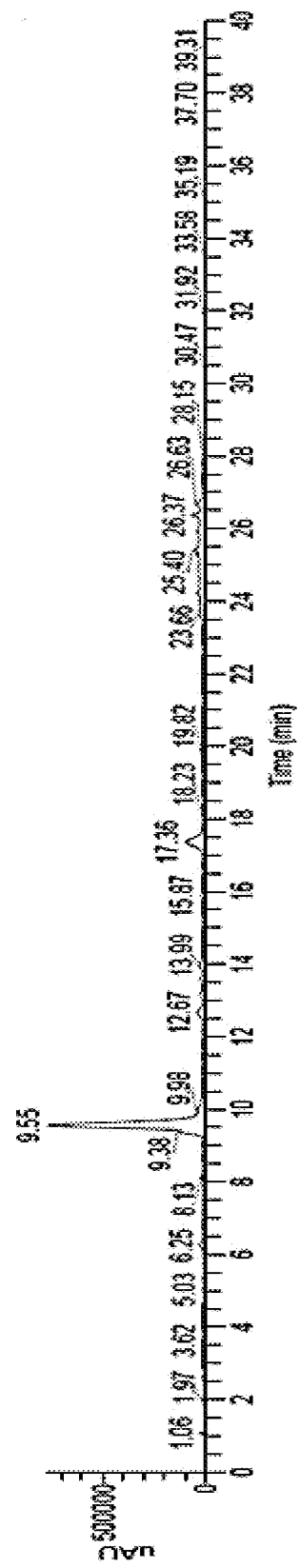
FIG. 3B shows the positive mode LC/MS spectrum of 5-methyl-benzol[1,3]dioxole-4,7-diol.
Figure 3C:
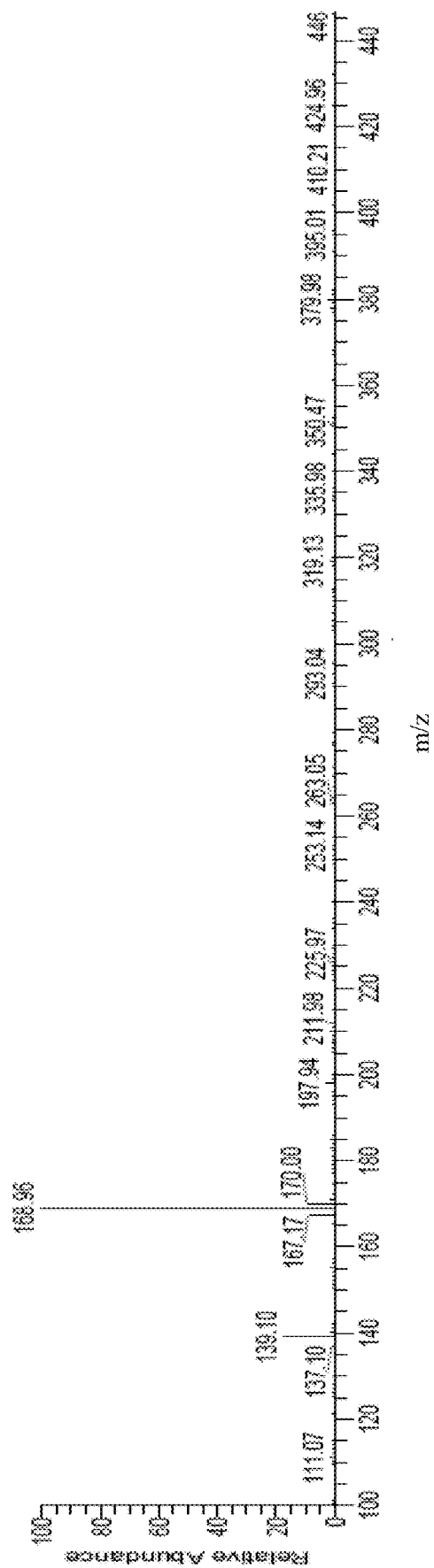
FIG. 3C shows the MS spectrum of the positive mode LC/MS of the fifth *Antrodia cinnamomea* extract.

The positive mode LC/MS spectrum of the fifth *Antrodia cinnamomea* extract is shown as FIG. 3A; wherein the spectrum exhibits peaks at retention time of 1.16 minute, 1.96 minute, 2.62 minute, 5.49 minute, 6.31 minute, 8.25 minute, 9.66 minute, 13.07 minute, 13.71 minute, 15.93 minute, 18.30 minute, 21.30 minute, 23.02 minute, 23.73 minute, 25.49 minute, 25.98 minute, 30.17 minute, 31.02 minute, 33.24 minute, 35.29 minute, 35.83 minute, 38.37 minute, and 39.93 minute. The spectrum shown in FIG. 3A was highly matched with that of the standard sample, 5-methyl-benzol[1,3]dioxole-4,7-diol. That is to say, the component of 9.66 minute retention time of FIG. 3A was deemed as the expected compound: 5-methyl-benzol[1,3]dioxole-4,7-diol.

Figure 4A:
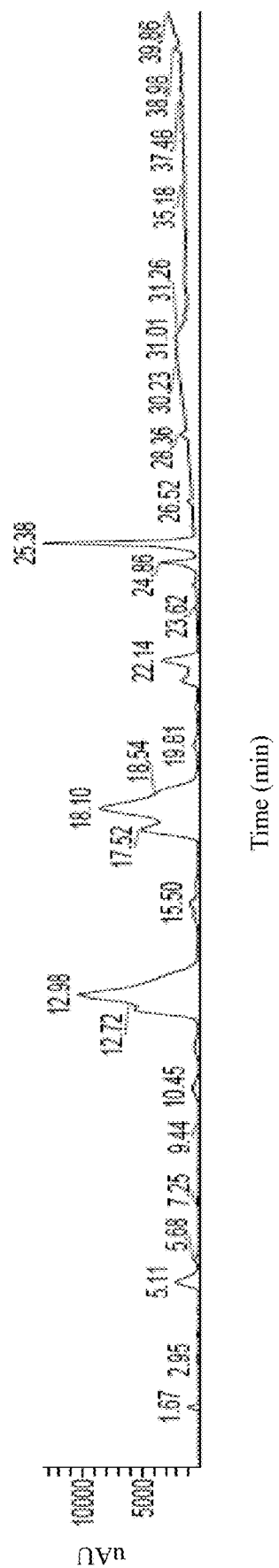
FIG. 4A shows the LC spectrum of the positive mode LC/MS of the sixth *Antrodia cinnamomea* extract.
Figure 4B:
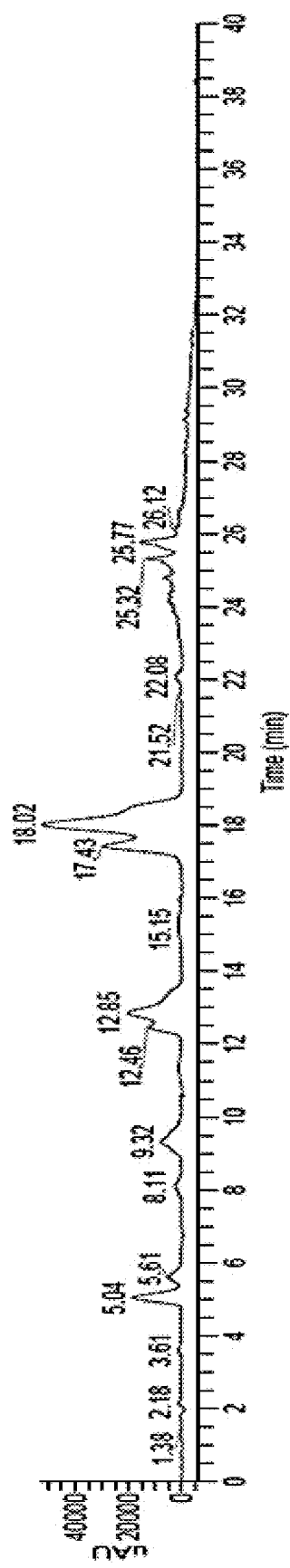
FIG. 4B shows the positive mode LC/MS spectrum of 2,4-dimethoxy-6-benzene-1,3-diol.
Figure 4C:
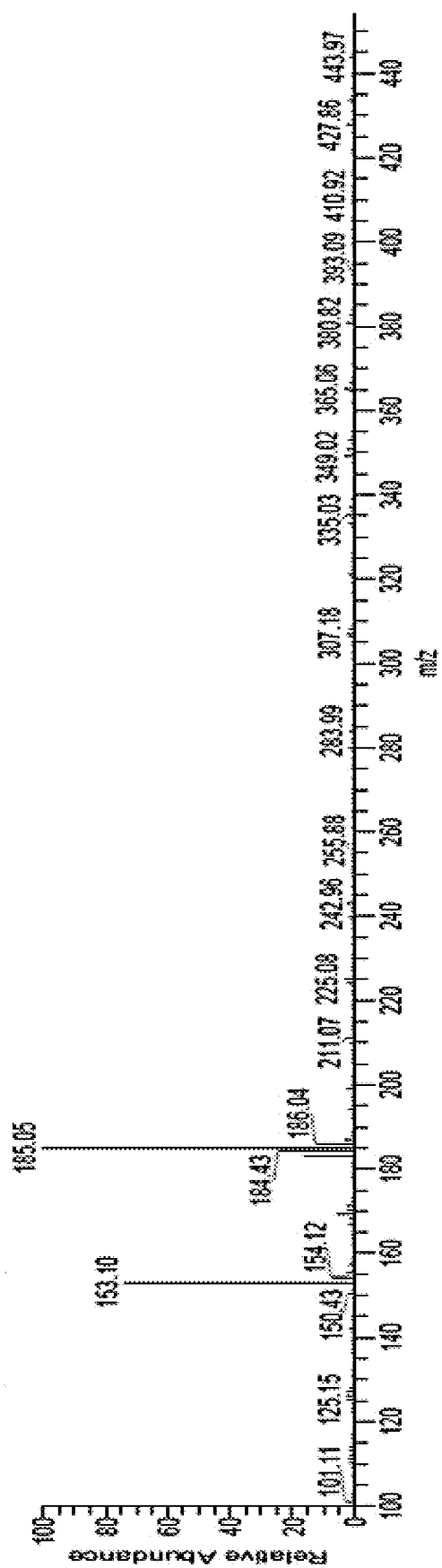
FIG. 4C shows the MS spectrum of the positive mode LC/MS spectrum of the sixth *Antrodia cinnamomea* extract.

The positive mode LC/MS spectrum of the sixth *Antrodia cinnamomea* extract is shown as FIG. 4A; wherein the spectrum exhibits peaks at retention time of 1.67 minute, 2.95 minute, 5.11 minute, 5.68 minute, 7.25 minute, 9.44 minute, 10.45 minute, 12.72 minute, 12.98 minute, 15.50 minute, 17.52 minute, 18.10 minute, 18.54 minute, 19.81 minute, 22.14 minute, 23.62 minute, 24.86 minute, 25.38 minute, 26.52 minute, 28.36 minute, 30.23 minute, 31.01 minute, 31.26 minute, 35.18 minute, 37.48 minute, 38.98 minute, and 39.86 minute. The spectrum shown in FIG. 4A was highly matched with that of the standard sample, 2,4-dimethoxy-6-benzene-1,3-diol (FIG. 4B). That is to say, the component of 12.98 minute retention time of the spectrum in FIG. 4C was deemed as the expected compound: 2,4-dimethoxy-6-benzene-1,3-diol.

(3) NMR Analysis.

The 9.66 minute retention time component of the fifth *Antrodia cinnamomea* extract and the 12.98 minute retention time component of the sixth *Antrodia cinnamomea* extract were further analyzed. NMR analysis was performed for the component of the fifth *Antrodia cinnamomea* extract using Bruker DMX-500 SB Spectrometer (500 MHz; $CD_3OD$).

Figure 3D:
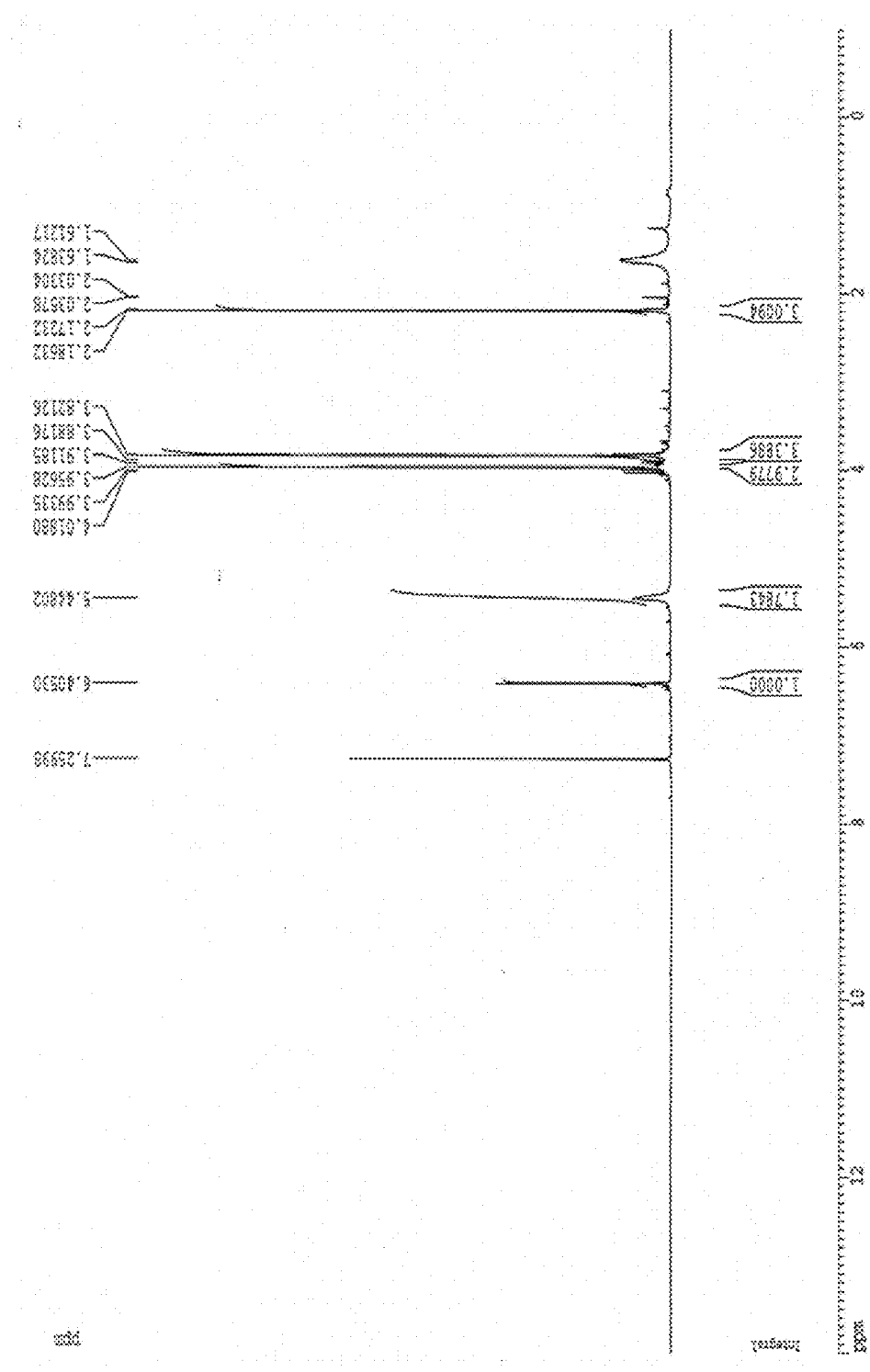
FIG. 3D shows the $^1$H NMR spectrum of 5-methyl-benzol[1,3]dioxole-4,7-diol.

The 9.66 minute retention time component of the fifth *Antrodia cinnamomea* extract exhibited NMR spectrum as shown in FIG. 3D and was determined as 5-methyl-benzol[1,3]dioxole-4,7-diol based on the indicated chemical shift value.

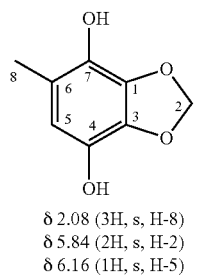

δ 2.08 (3H, s, H-8)
δ 5.84 (2H, s, H-2)
δ 6.16 (1H, s, H-5)

Figure 4D:
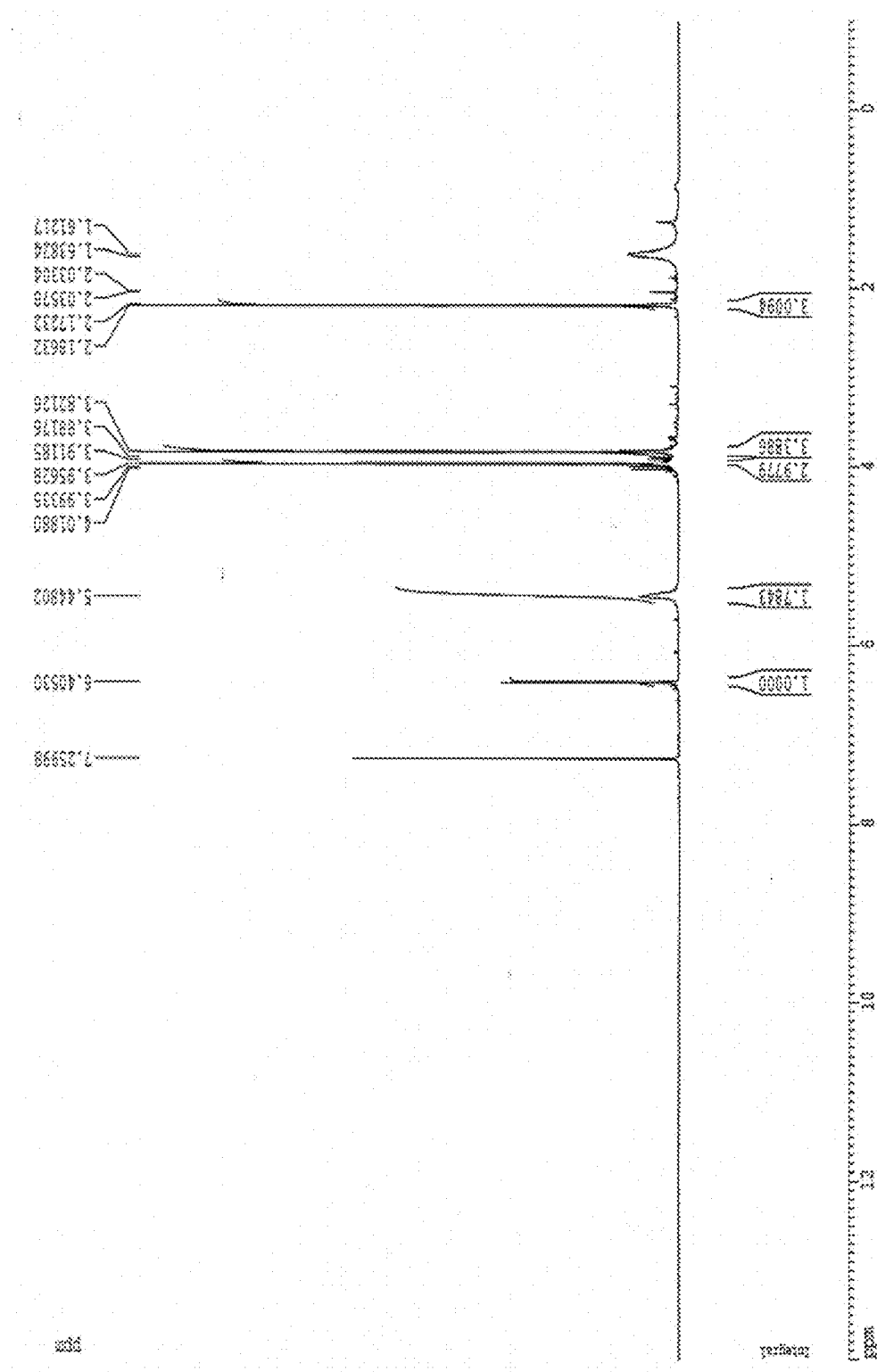
FIG. 4D shows the $^1$H NMR spectrum of 2,4-dimethoxy-6-benzene-1,3-diol.

Another NMR analysis was performed for the component of the sixth *Antrodia cinnamomea* extract using Varian UNITY INOVA 500 spectrometer (500 MHz; $CDCl_3$). The 12.98 minute retention time component of the sixth *Antrodia cinnamomea* extract exhibited NMR spectrum as shown in FIG. 4D and was determined as 2,4-dimethoxy-6-benzene-1,3-diol based on the indicated chemical shift value.

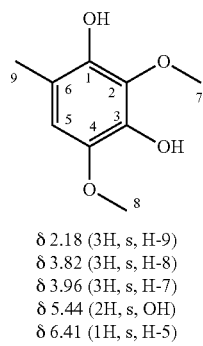

δ 2.18 (3H, s, H-9)
δ 3.82 (3H, s, H-8)
δ 3.96 (3H, s, H-7)
δ 5.44 (2H, s, OH)
δ 6.41 (1H, s, H-5)

Experiment 5: Activity of the *Antrodia cinnamomea* Extract on Anti-Fibrosis.

[MTT Killing Assay]

First of all, rat stellate cell (HSC-T6) was cultured in 75T cell culture flask for 2 to 3 days (5% $CO_2$; 37° C.). Then, cells were collected using 0.5% trypsin and put into centrifugation to harvest the cells. The cells were then inoculated into 96-well plate (1.5 to $2.0 \times 10^4$ cells/well) and cultured for overnight (5% $CO_2$; 37° C.). Afterwards, various concentration of *Antrodia cinnamomea* extracts were added for co-culture for another 24 or 48 hours. Then, MTT (3-(4,5-Dimethylthiazol-2-yl)-2,5-diphenyltetrazolium bromide) assay was performed to determine the cell activity. Briefly, each well of the culture plate was added of 12 μl MTT reagent (5 mg/ml) and cultured for 2.5 to 3.0 hours at 37° C. incubator. After removing the MTT reagent, 100 μl of lysis buffer was added for each well. The lysis buffer comprises 50% of N,N dimethylformamide (N,N-DMF) and 20% of sodium dodecyl sulfate (SDS). The 96-well plate was again put into 37° C. incubator until the purple crystalline material was dissolved from cells. Last, the absorbance was detected at 570 nm using spectrometer. The killing ratio of the *Antrodia cinnamomea* extract was calculated in comparison with the un-treated control group. Table 1 below shows the $IC_{50}$ of the *Antrodia cinnamomea* extract of the present disclosure on rat stellate cells.

TABLE 1 the $IC_{50}$ of the *Antrodia cinnamomea* extract of the present disclosure on rat stellate cells.

| Extract of the present disclosure | $IC_{50}$ (μg/mL) |
| --- | --- |
| the first extract | 157.8 |
| the second extract | 198.6 |
| the fifth extract | 2.2 |
| the sixth extract | 19.7 |

[Sirius Red Staining Assay]

Sirius Red Staining Assay was performed to test the effect of the first *Antrodia cinnamomea* extract and the second *Antrodia cinnamomea* extract of the present disclosure on the fibrin amount inside rat stellate cells. The rat stellate cells were treated with various concentration of *Antrodia cinnamomea* extract (25, 50, and 100 μg/ml) for 24 hours. Then, the cells were fixed by methanol and stored at −20° C. overnight. The cells were washed by PBS twice and cultured for 3 hours with 0.1% of PSR stain agent at room temperature. Afterwards, additional stain agent was removed by washing with 0.1% formic acid three times. Then, 0.1 N sodium hydroxide was added (100 μl/per well) to dissolve the stain agent binding with fibrin. Last, the absorbance was detected at 540 nm using Dynex Technologies MRX spectrophotometer. The ratio of fibrin amount in the experimental group to the un-treated control group was calculated.

Figure 5:
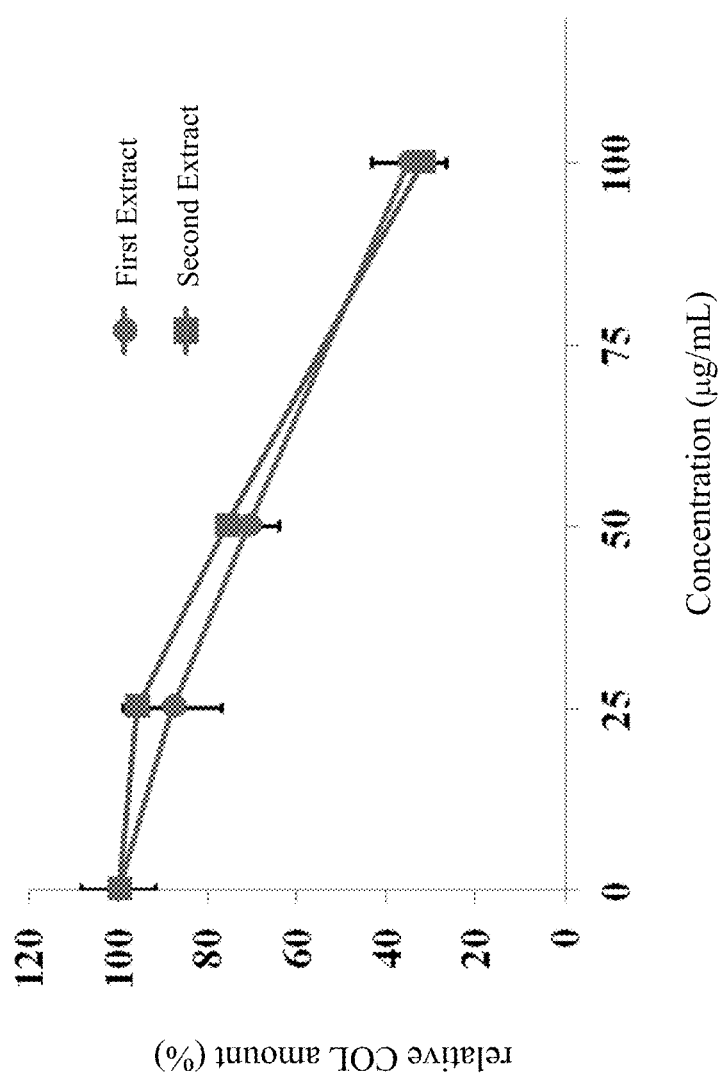
FIG. 5 shows the result of the Sirius Red Staining Assay in Experiment 4.

The data in FIG. 5 shows the relative fibrin amount (relative COL amount) of each experimental group based on the untreated control group. The results exhibits that stellate cells, treated with the first *Antrodia cinnamomea* extract or the second *Antrodia cinnamomea* extract of the present disclosure, comprised lower fibrin, especially in the 100 μg/ml group, whose fibrin amount was just 30% of that of the control group.

Experiment 6: Preparation of the Pharmaceutical Composition Comprising the *Antrodia cinnamomea* Extract.

The *Antrodia cinnamomea* extract of the present disclosure and additives were mixed in sterile water according to the ratio disclosed in Table 2 so as to prepare the pharmaceutical compositions of the present disclosure in liquid formulation. The prepared pharmaceutical compositions were stored at 4° C. for future use.

TABLE 2

| | Components and concentration (wt %) thereof of the pharmaceutical composition of the present disclosure. | | | | | | | | | | | | | | | | |
|---|---|---|---|---|---|---|---|---|---|---|---|---|---|---|---|---|---|
| | Sample # | | | | | | | | | | | | | | | | |
| | 1 | 2 | 3 | 4 | 5 | 6 | 7 | 8 | 9 | 10 | 11 | 12 | 13 | 14 | 15 | 16 | 17 |
| the first extract | 5 | 0 | 0 | 0 | 0 | 0 | 50 | 0 | 0 | 0 | 0 | 0 | 0 | 0 | 10 | 10 | 0 |
| the second extract | 0 | 5 | 0 | 0 | 0 | 0 | 0 | 50 | 0 | 0 | 0 | 0 | 0 | 0 | 10 | 0 | 10 |
| the third extract | 0 | 0 | 5 | 0 | 0 | 0 | 0 | 0 | 95 | 0 | 0 | 0 | 0 | 0 | 0 | 0 | 0 |
| the fourth extract | 0 | 0 | 0 | 5 | 0 | 0 | 0 | 0 | 0 | 95 | 0 | 0 | 0 | 0 | 0 | 0 | 0 |
| the fifth extract | 0 | 0 | 0 | 0 | 5 | 0 | 0 | 0 | 0 | 0 | 50 | 0 | 95 | 0 | 0 | 50 | 0 |
| the sixth extract | 0 | 0 | 0 | 0 | 0 | 5 | 0 | 0 | 0 | 0 | 0 | 50 | 0 | 95 | 0 | 0 | 50 |
| benzyl alcohol | 5 | 5 | 5 | 5 | 5 | 5 | 5 | 5 | 5 | 5 | 5 | 5 | 5 | 5 | 5 | 5 | 5 |

What is claimed is:

1. A method for preventing and/or treating liver fibrosis: comprising administering a subject in need an effective amount of Formula (I) compound:

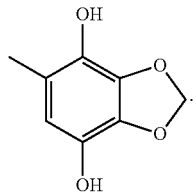

2. The method of claim 1, wherein the effective amount is sufficient to inhibit the activity of a stellate cell.

3. The method of claim 1, wherein the Formula (I) compound is formulated as a pharmaceutical composition; wherein the pharmaceutical composition further comprises a pharmaceutically acceptable additive.

4. The method of claim 3, wherein the pharmaceutical composition is formulated as tablet, capsule, injection, powder, granule, or oral solution.

5. The method of claim 3, wherein the pharmaceutically acceptable additive comprises: carrier, excipient, preservative, diluent, filler, binding agent, disintegrant, absorption accelerator, sweetener, or a combination thereof.

6. The method of claim 1, wherein the effective amount is 0.02 to 2.0 g/60 kg body weight/day.

* * * * *